United States Patent [19]

Ichikawa et al.

[11] Patent Number: 5,246,634
[45] Date of Patent: Sep. 21, 1993

[54] PROCESS FOR PRODUCING INTRAOCULAR LENS

[75] Inventors: Makoto Ichikawa; Yoshiyuki Ikeda, both of Nagoya; Kazuhiko Nakada, Aichi, all of Japan

[73] Assignee: Menicon Co., Ltd., Japan

[21] Appl. No.: 822,918

[22] Filed: Jan. 21, 1992

[51] Int. Cl.⁵ .......................................... B29D 11/00
[52] U.S. Cl. ................................ 264/1.7; 264/1.4; 264/22; 264/246; 264/255; 264/2.7; 264/157; 264/297.878; 351/162; 351/172; 351/177
[58] Field of Search .................. 264/1.4, 1.7, 2.7, 250, 264/255, 299, 22, 246, 157, 78, 297.8; 351/162, 170, 177, 161, 172

[56] References Cited

U.S. PATENT DOCUMENTS

| | | | |
|---|---|---|---|
| 3,454,332 | 7/1969 | Siegel | 351/177 |
| 3,560,598 | 2/1971 | Neefe | 264/1.4 |
| 3,712,718 | 1/1973 | Le Grand et al. | 351/177 |
| 4,460,523 | 7/1984 | Neefe | 351/177 |
| 4,701,288 | 10/1987 | Cook et al. | 264/1.4 |
| 4,710,327 | 12/1987 | Neefe | 351/162 |
| 4,774,036 | 9/1988 | LeMaster et al. | 264/1.7 |
| 5,089,180 | 2/1992 | Dunks et al. | 264/1.7 |

FOREIGN PATENT DOCUMENTS

| | | |
|---|---|---|
| 0331457 | 9/1989 | European Pat. Off. |
| 0353651 | 2/1990 | European Pat. Off. |
| 62-161360 | 7/1987 | Japan |
| 2-7954 | 1/1990 | Japan |
| 2181355 | 4/1987 | United Kingdom |

Primary Examiner—Jeffrey Thurlow
Assistant Examiner—Mathieu Vargot
Attorney, Agent, or Firm—Parkhurst, Wendel & Rossi

[57] ABSTRACT

A process of producing a one-piece intraocular lens in which the lens includes an optical portion and at least one support portion produced integrally with each other, the process including the steps of (a) forming a first polymerized material into a lens blank, the lens blank including a convex portion to provide the optical portion of the intraocular lens, and a flange portion surrounding the convex portion, (b) applying, to one of opposite surfaces of the flange portion on a side of a convex surface of the convex portion, a monomer composition which is polymerizable to produce a second polymerized material different from the first polymerized material, the monomer composition including at least one polymerizable monomer, (c) polymerizing the monomer composition on the flange portion to provide a double-layer portion defined by the flange portion and the second polymerized material produced integrally with the lens blank from the monomer composition, and (d) forming the convex portion and double-layer portion into the optical portion and at least one support portion of the intraocular lens, respectively.

16 Claims, 3 Drawing Sheets

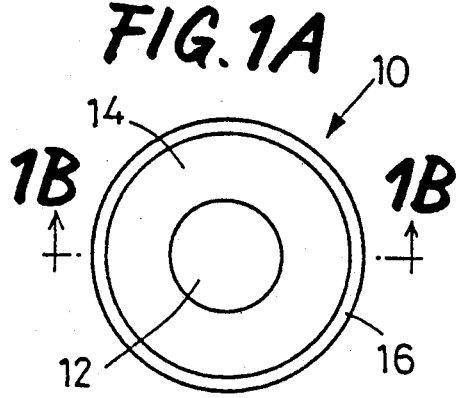
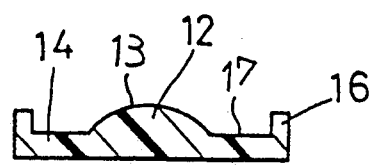
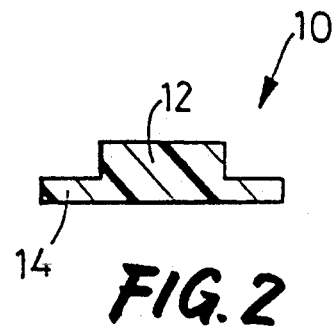
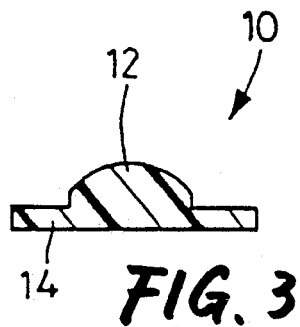
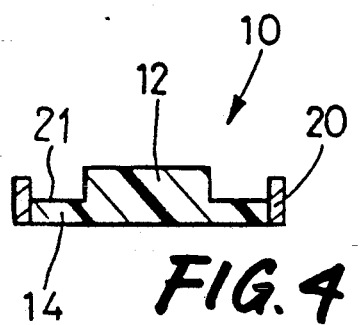

PROCESS FOR PRODUCING INTRAOCULAR LENS

BACKGROUND OF THE INVENTION

1. Field of the Invention

The present invention relates to a process of producing a one-piece intraocular lens in which an optical portion and a support portion of the lens are produced integrally and simultaneously with each other, wherein the optical and support portions are formed of different materials.

2. Related Art Statement

An intraocular lens includes an optical portion serving as an optical lens, and a support portion for attaching the optical portion to a suitable site in an eye of a patient. Conventionally, there are known intraocular lenses having two- or three-pieces in which an optical portion and a support portion are produced separately from each other and subsequently the support portion is fixed to the optical portion. Further, one-piece intraocular lenses are known in which an optical portion and a support portion are produced integrally with each other.

In addition, there is well known in the art an intraocular lens of a type in which an optical portion and a support portion are formed of different materials. For example, the optical and support portions are produced by polymerization of different monomer compositions including different polymerizable monomers, different compounding agents and/or additive agents, or different amounts of those agents. More specifically, the optical portion may be formed of a colorless, transparent polymerizable material and simultaneously the support portion may be formed of a polymerizable material containing a coloring agent, so that the support portion can easily be identified when the intraocular lens is inserted to patient's eye. In addition, it is known to add different amounts of crosslinking agent to respective materials for optical and support portions of an intraocular lens to provide different degrees of flexibility for the two portions. In this way, the optical and support portions possess different optical or physical properties with respect to each other as required.

Japanese Patent Application laid open under Publication No. 2-7954 (corresponding to U.S. patent application No. 07/164,140) discloses a process of producing a one-piece intraocular lens wherein the optical and support portions thereof are formed of different materials. More specifically, the Japanese document teaches a process of producing an intraocular lens in which only the support portion thereof is colored. In the disclosed process, first, a colorless, transparent plastic material is used to provide a central portion for a lens blank. Subsequently a liquid, colored plastic material, is located around the central colorless portion, and then is polymerized to harden the outer colored portion. Thus, a lens blank is produced in which the central colorless portion and the outer colored portion are integrally combined with each other. Alternatively, a colored material first is formed into an outer portion for a lens blank and subsequently a colorless transparent material is poured into a central hole of the colored portion and is then polymerized, so as to produce a lens blank similar to the above-indicated first lens blank (i.e. lens blank in which the colorless central and colored outer portions thereof are integrally connected with each other). A desired intraocular lens is obtained by forming the colorless central and colored outer portions of the lens blank into the optical and support portions of the lens, respectively.

However, the above-indicated second process, in which the central portion of a lens blank is formed within a central hole in the colored outer portion, may suffer from a problem that distortion occurs to the central portion thus formed. That is, the optical properties of an intraocular lens as an end product may adversely be affected. Meanwhile, the above-indicated first process, in which the colored outer portion of a lens blank is formed by polymerization around the colorless central portion, may suffer from a problem that it is extremely difficult to align the center of the colorless central portion with the center of the lens blank as a whole. This problem causes the "color misalignment" problem that an intraocular lens as an end product has colored material in the optical portion or has colorless material in the support portion, because the lens blank is worked or machined into the lens by referencing the center of the entire lens blank as the center for the shape working.

Another process of producing a one piece-type intraocular lens whose support portion is colored, is disclosed in Japanese Patent Application laid open under Publication No. 62-161360 (corresponding to U.S. patent application No. 06/787,495). In the disclosed process, a colored plastic material is located around an optical member formed of a colorless transparent plastic material, and subsequently heat is applied to fuse the optical member and the plastic material into an integral member, that is, a lens blank. A final lens is obtained from this lens blank. This process may suffer from the problem that it is very difficult to align the center of the optical member with the center of the entire lens blank (i.e., the above-identified "color misalignment" problem).

As is understood from the foregoing description, the conventional processes have the problem that the optical properties of an intraocular lens produced thereby are deteriorated due to distortion occurring to the optical portion of the lens, or invasion of the material for the support portion of the lens into that for the optical portion thereof. In addition, the known processes suffer from the problem that the support portion of an intraocular lens fails to have satisfactory physical properties due to invasion of the material for the optical portion of the lens into that for the support portion.

SUMMARY OF THE INVENTION

It is therefore an object of the present invention to provide a process of producing a one-piece intraocular lens in which the optical and support portions thereof are formed of different materials, which process is free from the problems of distortion of the optical portion, misalignment of the center of the optical portion, or "color misalignment".

The above object has been achieved by the present invention, which provides a process of producing a one-piece intraocular lens in which the lens includes an optical portion and at least one support portion produced integrally with each other, the process comprising the steps of (a) forming a first polymerized material into a lens blank, the lens blank including a convex portion providing the optical portion of the intraocular lens, and a flange portion surrounding the convex portion, (b) applying, to one of opposite surfaces of the flange portion on a side of a convex surface of the convex portion, a monomer composition which is polymerizable to produce a second polymerized material different from the first polymerized material, the monomer composition including at least one polymerizable monomer, (c) polymerizing the monomer composition on the flange portion to provide a double-layer portion having the flange portion and the second polymerized material produced integrally with the lens blank from the monomer composition, and (d) forming the convex portion and double-layer portion of the lens blank, into the optical portion and at least one support portion of the intraocular lens, respectively.

In the intraocular lens producing process described above, an unreacted polymerizable material is applied to the flange portion of the lens blank formed of the first polymerized material, and subsequently is polymerized on the flange portion to produce a second polymerized material. Consequently, a layer of the second polymerized material superposed on the flange portion is integrally combined with the outer periphery of the convex portion of the lens blank. According to the present invention, the convex portion providing the optical portion of the final intraocular lens is polymerized first. Therefore, the present process does not distort the optical portion of the lens, and the final intraocular lens has stable optical properties.

In the present producing process, the lens blank includes the flange portion surrounding the convex portion such that the flange and convex portions are integral with each other, and therefore the position of the convex portion relative to the flange portion cannot be changed. On the flange portion, a superposed layer is formed of the second polymerized material. Thus, the center of the convex portion cannot be changed relative to the center of the entire lens blank after the formation of the superposed layer on the flange portion. Thus, the present process is free from the problem of misalignment of the center of the optical portion of the lens. That is, the present process insures that the center of working or machining of a lens blank into a lens product is easily specified on the blank even after the second polymerized material has been formed on the flange portion. Therefore, the convex portion of the first polymerized material is accurately formed into the optical portion of the lens product, while the superposed layer of the second polymerized material on the flange portion is accurately formed into the support portion of the lens. Consequently, the present process does not suffer from the problem of invasion of the colored material for the support portion into the colorless material for the optical portion, or invasion of the colorless material for the optical portion into the colored material for the support portion, and therefore is free from the conventionally encountered "color misalignment" problem.

BRIEF DESCRIPTION OF THE DRAWINGS

The above and optional objects, features and advantages of the present invention will be better understood by reading the following detailed description of the present preferred embodiments of the invention when considered in conjunction with the accompanying drawings, in which:

FIG. 1A is a plan view of a lens blank;

FIG. 1B is a cross-sectional view taken along line 1B—1B of FIG. 1A, of the lens blank of FIG. 1A;

FIG. 2 is a cross-sectional view corresponding to FIG. 1B, of another lens blank;

FIG. 3 is a cross-sectional view corresponding to FIG. 1B, of yet another lens blank;

FIG. 4 is a cross-sectional view corresponding to FIG. 1B, of a different lens blank;

DETAILED DESCRIPTION OF THE INVENTION

Figure 5:
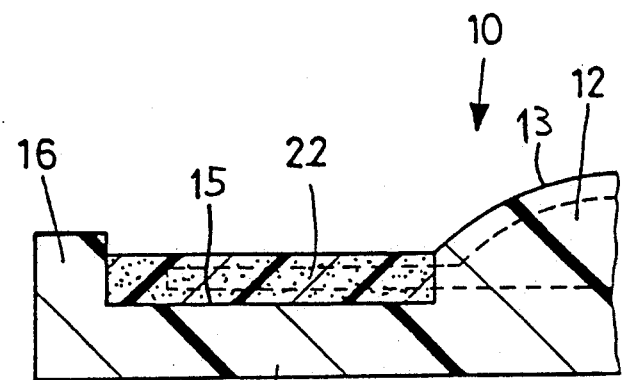
FIG. 5 is a cross-sectional view showing a superposed layer formed on a flange portion of the lens blank of FIG. 3.

In the present invention, the first and second polymerized materials used for a lens blank and a superposed layer on the flange portion of the lens blank, respectively, are formed of different monomer compositions containing different polymerizable monomers, different sorts of compounding agents and/or additive agents, or different amounts (or contents) of those agents. Therefore, the first and second polymerized materials have different optical or physical properties. It is preferred that the first polymerized material be formed of a polymerizable composition suitable for the optical portion of an intraocular lens while the second polymerized material be formed of a polymerizable composition suitable for the support portion of the lens. In this preferred case, an excellent intraocular lens whose optical and support portions have good optical or physical properties is obtained.

For example, the first polymerized material may be a colorless, transparent material formed of a polymerizable composition without a coloring agent, while the second polymerized material may be a colored material formed of a polymerizable composition containing a coloring agent. In this case, an intraocular lens is produced having a colorless and transparent optical portion and colored support portion.

The first or second polymerized material may be formed of various polymerizable compositions which conventionally have been used for providing hard or soft materials for intraocular lenses.

For example, a suitable hard or soft material may be obtained by polymerizing one or more of the following polymerizable monomers (hereinafter, regarding the expression of an acrylate or an acryl derivative, the term "(meth)acrylate" or "(meth)acryl-" is used to indicate two sorts of acrylates, i.e., acrylate and methacrylate, or two sorts of groups, i.e., acryl- and methacryl-, respectively): straight chain, branched chain, or cycloalkyl (meth)acrylates such as methyl (meth)acrylate, ethyl (meth)acrylate, propyl (meth)acrylate, n-butyl (meth)acrylate, tert-butyl (meth)acrylate, isobutyl (meth)acrylate, n-pentyl (meth)acrylate, tert-pentyl (meth)acrylate, hexyl (meth)acrylate, 2-methylbutyl (meth)acrylate, heptyl (meth)acrylate, octyl (meth)acrylate, 2-ethylhexyl (meth)acrylate, nonyl (meth)acrylate, decyl (meth)acrylate, dodecyl (meth)acrylate, stearyl (meth)acrylate, cyclopentyl (meth)acrylate, and cyclohexyl (meth)acrylate; fluorine-containing (meth)acrylate derivatives; silicon-containing (meth)acrylate derivatives; styrene and its derivatives; fluorine-containing styrene derivatives; N-vinyllactam and its derivatives; hydroxyl group-containing (meth)acrylate derivatives such as hydroxyethyl (meth)acrylate, hydroxypropyl (meth)acrylate, hydroxybutyl (meth)acrylate, dihydroxypropyl (meth)acrylate, dihydroxybutyl (meth)acrylate, diethylene glycol mono(meth)acrylate, triethylene glycol mono(meth)acrylate, and dipropylene glycol mono(meth)acrylate; (meth)acrylamide and its derivatives such as (meth)acrylamide, N-methyl(meth)acrylamide, N-ethyl(meth)acrylamide, N-hydroxyethyl(meth)acrylamide, N,N-dimethyl(meth)acrylamide, N, N-diethyl(meth)acrylamide, and N-ethylaminoethyl(meth)acrylamide.

From the above-indicated monomers, one or more sorts of monomers may be selected and used. Alternatively, it is possible to obtain a "macromonomer" by polymerization of one or more monomers and use the macromonomer as a constituent of a polymerizable composition for the first or second polymerized material. Depending upon desired properties of the first or second polymerized material, a suitable monomer or monomers and, if appropriate, suitable proportions of the monomers may be selected and specified.

A commonly used polymerizable ultraviolet absorbing agent and/or a polymerizable dye may be used as a polymerizable constituent or constituents of a polymerizable composition for the first or second polymerized material.

Although according to the principle of the present invention it is possible to use as the first or second polymerized material a polymerized material without having crosslinking structure therein, it is preferred from the standpoint of shape stability to use, in particular as the first polymerized material providing the optical portion of the intraocular lens, a polymerized material which has crosslinking structure therein.

The following crosslinking agents are preferably added to the polymerizable composition for the first or second polymerized material: 4-vinylbenzyl (meth)acrylate, 3-vinylbenzyl (meth)acrylate, ethylene glycol di(meth)acrylate, diethylene glycol di(meth)acrylate, triethylene glycol di(meth)acrylate, propylene glycol di(meth)acrylate, dipropylene glycol di(meth)acrylate, allyl (meth)acrylate, and vinyl (meth)acrylate. From these agents, one or more sorts of crosslinking agents may be selected and used. It is possible to use, as a crosslinking agent, a macromonomer containing two or more polymerizable groups in the molecule thereof. It is preferred that the polymerizable composition for the first or second polymerized material contains 0.5 to 15 parts by weight, more preferably, 1 to 10 parts by weight, of the crosslinking agent per 100 parts by weight of all the polymerizable constituents of the composition. If the content of the crosslinking agent is higher than the upper limit, 15 parts by weight, the polymerized material produced suffers from brittleness and therefore weakness against stress caused by mechanical shock applied thereto. Meanwhile, if the content of the crosslinking agent is lower than the lower limit, 0.5 part by weight, the crosslinking agent fails to exhibit satisfactory crosslinking effect.

In addition to the crosslinking agent, one or more sorts of known compounding agents and/or additive agents may be added to the polymerizable composition for the first or second polymerized material. Different polymerizable compositions for producing the first and second polymerized materials are produced by uniformly mixing one or more polymerizable monomers, a crosslinking agent, a compounding agent, and/or an additive agent.

The coloring agent added to the polymerizable composition for the first or second polymerized material may be a well known additive agent. A coloring agent is commonly added to the polymerizable composition for the second polymerized material, so as to allow a doctor easily to recognize the support portion of an intraocular lens to be implanted in a patient's eye. According to the present invention, coloring agents are not limited to specific ones, although the coloring agents are required to bio-compatible. Any known dye or pigment may be used as a coloring agent. Preferable coloring agents are as follows: coloring matters used in the field of food and medicine, such as C.I. Acid Red 26 and C.I. Food Blue 2; direct dyes such as C.I. Direct Blue 237 and C.I. Direct Yellow 8; acid dyes such as C.I. Acid Blue 29 and C.I. Acid Black 2; basic dyes such as C.I. Basic Blue 5 and C.I. Basic Violet 1; vat dyes such as C.I. Vat Blue 18 and SOLUBILIZED C.I. Vat Blue 1; solvent dyes such as C.I. Solvent Violet 13 and C.I. Solvent Green 3; and disperse dyes such as C.I. Pigment Blue 15. In particular, the polymerizable dyes disclosed in Japanese Patent Application laid open under Publication No. 1-299560 are suitable for an intraocular lens, because those dyes are securely combined with the polymerized material.

From the above indicated coloring agents, one or more are selected and added to the polymerizable composition for the first or second polymerized material. It is preferred that the polymerizable composition contain 0.01 to 30 parts by weight of the coloring agent. If the content of the coloring agent is below the lower limit, 0.01 parts by weight, the color produced thereby becomes too light. Meanwhile, if the content of the coloring agent exceeds the upper limit, 30 parts by weight, the material is over-saturated. In the latter case, the coloring agent may migrate from the lens to the patient's tissue. In the case where a coloring agent which is hardly soluble or disperseable to the polymerizable composition, it is possible additionally to use a surface active agent and/or dispersing agent for promoting solution or dispersion.

Furthermore, a suitable polymerization initiator is added to the polymerizable composition thus prepared for the first or second polymerized material. Conventional polymerization processes may be employed for polymerizing the polymerizable composition. For example, it is possible to employ a thermal or heat polymerization process in which a radical polymerization initiator such as azobisisobutyronitrile or azobisdimethylvaleronitrile is mixed with the polymerizable composition and subsequently the composition is gradually heated from room temperature to about 130° C. in ten and several hours, so as to effect polymerization of the composition. In addition, a photopolymerization process may be used in which a photopolymerization initiator such as benzoin or methylorthobenzoyl benzoate is added to the polymerizable composition and then the composition is irradiated by light having wavelengths corresponding to the absorption band of the initiator, so as to polymerize the composition. Alternatively, it is possible to combine the thermal polymerization and photopolymerization techniques to polymerize the polymerization composition for the first or second polymerized material. Out of commonly used polymerization initiators, one or more sorts of initiators is/are selected and used. It is preferred that the polymerizable composition contain 0.001 to 5 parts by weight, more preferably 0.01 to 2 parts by weight, of the polymerization initiator per 100 parts by weight of all the polymerizable constituents of the composition.

DETAILED DESCRIPTION OF THE PREFERRED EMBODIMENTS

In the process according to the present invention, first, the polymerizable composition for the first polymerized material is polymerized into the first polymerized material. The first polymerized is then formed into a lens blank which includes a convex portion providing the optical portion of an intraocular lens, and a flange portion surrounding the convex portion. Therefore, the intraocular lens as an end product has the optical portion which is free from distortion and accordingly possesses excellent optical properties.

The lens blank may be formed into a variety of configurations or shapes depending upon desired shapes of intended lens products (i.e., intraocular lenses). For example, a lens blank 10 shown in FIGS. 1A and 1B has a generally disc-like configuration. The lens blank 10 includes a convex portion 12 in a central portion thereof such that the convex portion 12 is concentric with the blank disc 10. The convex portion 12 has a partial spherical surface 13. The lens blank 10 further includes an annular flange portion 14 surrounding the outer periphery of the convex portion 12. Reference numeral 16 designates a continuous thick portion protruding from the outer periphery of the flange portion 14. The convex portion 12 and the continuous thick portion 16 cooperate with each other to define a generally annular groove 17 on the side of the part-spherical surface 13 of the convex portion 12. When the polymerizable composition for the second polymerized material is poured into the annular groove 17, the continuous thick portion 16 effectively prevents the composition from overflowing from the groove 17, thereby facilitating the pouring operation.

The convex portion 12 of the lens blank 10 may have a cylindrical shape with a circular plan surface as shown in FIG. 2, or a generally cylindrical shape with a partial spherical surface as shown in FIG. 3. Alternatively, the convex portion 12 may have a prismatic shape. The flange portion 14 is not required to have the annular configuration as shown in FIG. 1A. The flange portion 14 may be provided at only a location or locations along the outer periphery of the convex portion 12 where a support portion or portions 26 (FIG. 28) of the intraocular lens is/are to be formed.

Figure 9:
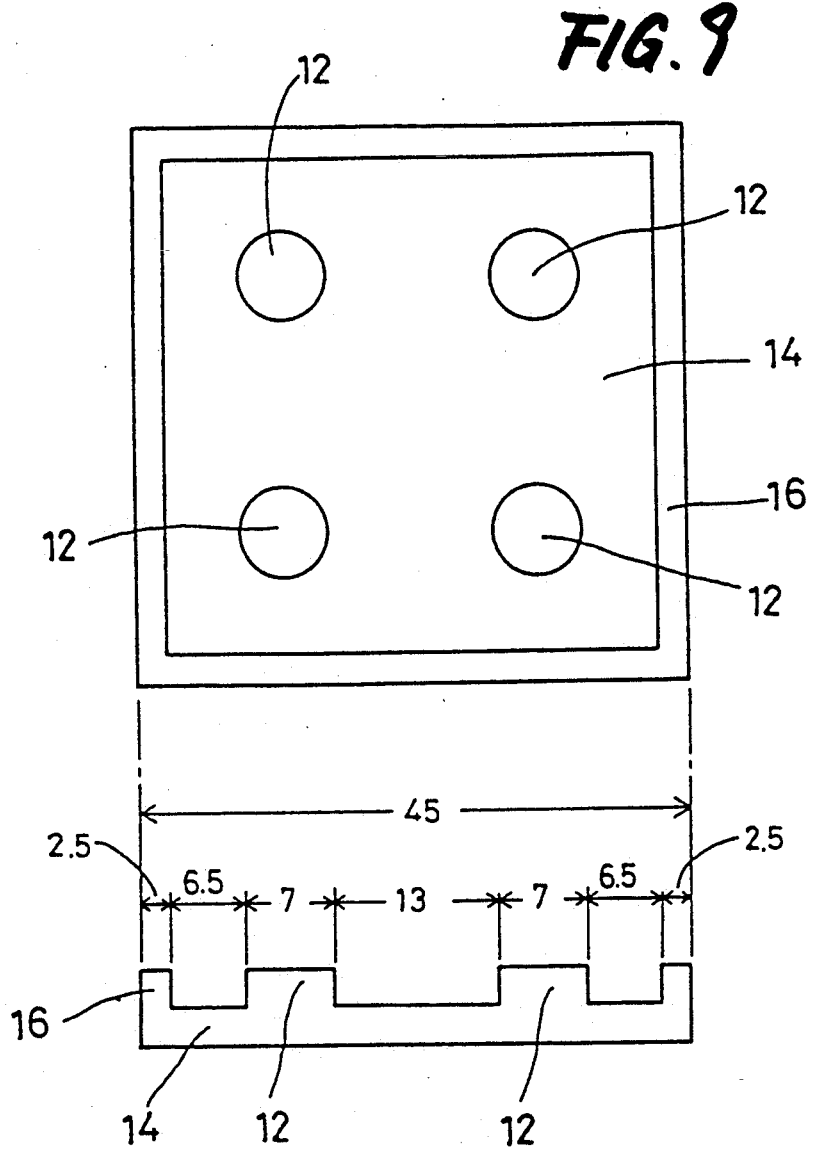
FIG. 9 is a view for explaining the configuration and dimensions of a lens blank as Invention Example 4.

The continuous thick portion 16 may be omitted as shown in FIG. 2 or 3. In this case, as shown in FIG. 4, a continuous frame member 20 may be applied to the outer periphery of the flange portion 14 of the lens blank 10, so that the convex portion 12 and the frame member 20 cooperate with each other to define a generally annular hollow space 21 on the side of the convex surface of the convex portion 12. This arrangement contributes to facilitating the application to the flange portion 14 of the polymerizable composition for the second polymerized material. Furthermore, as shown in FIG. 9, it is possible to form a lens blank including a plurality of convex portions 12 each of which provides an optical portion of an intraocular lens, and a plurality of flange portions 14 each of which surrounds a corresponding one of the convex portions 12. In this case, the polymerizable composition for the second polymerized material is applied onto the continuous flange portions 14 all at once, so that the second polymerized material is integrally combined with the lens blank 10. Before final shape working or machining (i.e., finishing), the convex portions 12 are separated from each other by cutting the continuous flange portions 14, so as to provide the independent convex portions 12, each of which subsequently is subjected to the finishing.

The lens blank 10, as shown in FIGS. 1 through 4, has dimensions slightly greater than those of an intraocular lens as an end product. If the dimensions of the lens blank 10 are excessively great, it takes much time and labor to remove unnecessary portions from the lens blank 10. It is therefore preferred that the convex portion 12 have a diameter or length of about 5 to 15 mm, that the lens blank 10 including the convex and flange portions 12, 14 except for the thick portion 16 have a diameter or length of about 10 to 20 mm, and that the height of the convex portion 12 as measured from the flange portion 14 be about 1 to 15 mm.

The polymerizable composition for the second polymerized material is applied to one of opposite surfaces is of the flange portion 14, that is, annular groove 17 (FIG. 1B) or annular hollow space 21 (FIG. 4). The surface 15 of the flange portion 14 is located on the side of the convex surface of the convex portion 12. The applied composition is polymerized by a suitable process to produce the second polymerized material, that is, a superposed layer 22 as shown in FIG. 5. The superposed layer 22 and the underlying flange portion 14 cooperate with each other to provide a double-layer portion. Since the applied composition is polymerized after partially having been impregnated into the convex portion 12 (and the flange portion 14), the superposed layer 22 is combined strongly with the convex portion 12, so that the superposed layer 22 is produced integrally with the convex portion 12. Since the convex portion 12 is stationary or fixed in position relative to the flange portion 14, the lens blank 10 is free from the problem of misalignment during the polymerization of the applied composition to the superposed layer 22.

Preferably, the composition for the second polymerized material is applied onto the flange portion 14 such that at least the top of the convex portion 12 is not covered by the applied composition or superposed layer 22, as shown in FIG. 5. In this situation, the convex portion 12 is easily distinguished from the superposed layer 22, and the center of working or machining of the lens blank 10 is easily found or specified based on the convex portion 12. In this case, the superposed layer 22 is formed such that the thickness of the layer 22 is smaller than the height of the convex portion 12. Usually, the thickness of the superposed layer 22 is selected at about 0.2 to 10.0 mm.

After the superposed layer 22 has been formed as described above, the lens blank 22 is subjected to shape working, including cutting and polishing to provide an intraocular lens as indicated in broken line shown in FIG. 5. Since the convex portion 12 is stationary in position relative to the entire lens blank 10, as described above, the center of working is easily identified on the convex portion 14 by grasping the outer periphery of the lens blank 10. (i.e., outer periphery of the flange portion 14 or thick portion 16). The center of working coincides with the center of the convex portion 12. In the case where the superposed layer 22 is formed with the top of the convex portion 12 being left exposed, the center of working is easily specified by grasping the convex portion 12.

Figure 6:
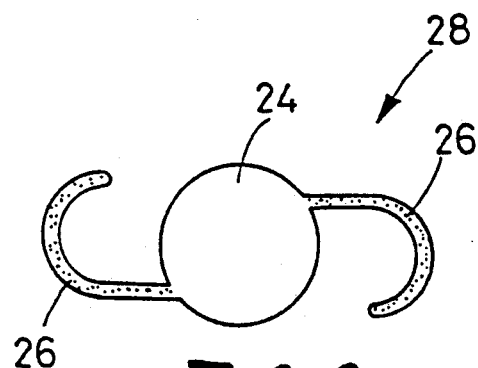
FIG. 6 is a plan view of an intraocular lens produced by the process according to the present invention.

The convex portion 12 and flange portion 14 of the lens blank 10 are respectively formed into an optical portion 24 and a pair of support portions 26 of an intraocular lens 28 as shown in FIG. 6. Each support portion 26 takes the form of a J-shaped hook. The shape working of the lens blank 10 is effected by using a precision instrument such as a commonly used fraise or milling machine.

As emerges from the foregoing description, in the intraocular lens producing process according to the present invention, the convex portion 12 corresponding to the optical portion of an intraocular lens, is securely connected with the superposed layer 22 corresponding to the support portion of the lens 28. Thus, the present process enables production of an excellent intraocular lens of a one-piece type in which the optical and support portions thereof are securely combined with each other, notwithstanding the optical and support portions are formed of different materials. In addition, since the convex portion 12 cannot be displaced relative to the entire lens blank 10 when the superposed layer 22 is formed on the lens blank 10, the lens blank 10 thus obtained does not suffer from the problem of misalignment of the center of the convex portion 12 with respect to the outer periphery of the lens blank 10. Therefore, based on the outer periphery of the lens blank 10 or, if appropriate, the convex portion 12, the center of working for forming the lens blank 10 into the end product 28, is easily identified. Thus, the present process is immune to the problem of "color misalignment" which has conventionally been encountered in the art. butyl (meth)acrylate, heptyl (meth)acrylate,

EXAMPLE 1

Figure 7:
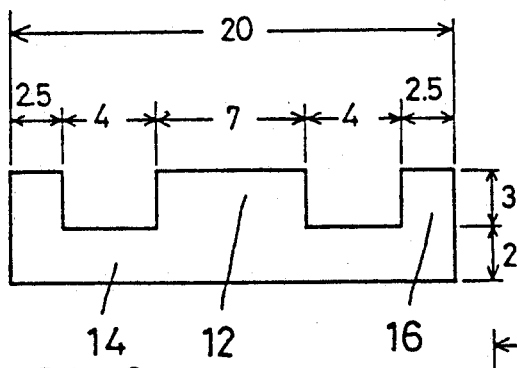
FIG. 7 is a view for explaining the configuration and dimensions of a lens blank as Invention Example 1 or Invention Example 2.

97 Parts by weight of methyl methacrylate and 3 parts by weight of diethylene glycol dimethacrylate are mixed with each other, and then are polymerized to produce a crosslinked polymethyl methacrylate as the first polymerized material. The polymerized material is formed into a disc-like plate having a 20 mm diameter. With the outer periphery of the plate (i.e., outer periphery of protruding portion 16 thereof) being grasped, the plate is formed into a disc-like lens blank having dimensions (unit: mm) as indicated in FIG. 7.

Meanwhile, 0.1% of C.I. Solvent Violet 13 (coloring agent) and 0.2% azobisisobutyronitrile (polymerization initiator) are added to methyl methacryate to thereby prepare a polymerizable composition for the second polymerized material. The composition is poured into an annular groove provided on flange portion 14 of the lens blank. The annular groove is covered with polyethylene film, and is kept at 50° C. for four hours. Thereafter, the temperature is raised from 50° C. to 110° C. in eight hours, so as to polymerize the composition and thereby form superposed layer 22 on the lens blank.

Subsequently, the center of the lens blank is identified based on the outer periphery of protruding portion 16, and this center is used as the center of working by a fraise. Thus, an intraocular lens including colored support portions is produced.

EXAMPLE 2

A lens blank is formed of the same first polymerized material as that used in Example 1. Meanwhile, 54 g of methyl methacrylate, 45 g of trifluoroethyl methacrylate, 1 g of ethylene glycol dimethacrylate (crosslinking agent), and 0.1 g of azobisisobutyronitrile (polymerization initiator) are mixed with each other to thereby prepare a polymerizable composition for the second polymerized material.

The thus prepared composition is poured into an annular groove provided on flange portion 14 of the lens blank. The annular groove is covered with polyethylene film, and is kept at 35° C. for 16 hours and then at 50° C. for six hours. Thereafter, the temperature is raised from 50° C. to 130° C. in 12 hours, so as to polymerize the composition.

Subsequently, the center of the lens blank is identified based on the outer periphery of convex portion 12, and this center is used as the center of working by a fraise. Thus, an intraocular lens including optical and support portions formed of different materials is produced.

EXAMPLE 3

Figure 8:
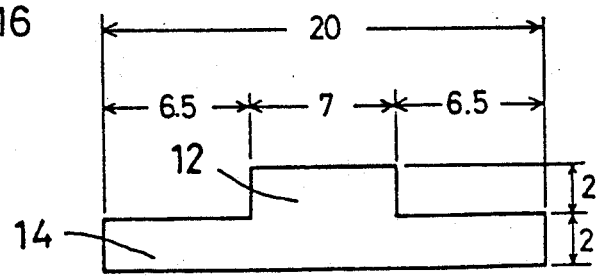
FIG. 8 is a view for explaining the configuration and dimensions of a lens blank as Invention Example 3.

A disc-like lens blank having dimensions (unit: mm) indicated in FIG. 8 is formed of the same first polymerized material as that used in Example 1. Subsequently, a cylindrical frame member (not shown) having an inner diameter of 20 mm and an axial length of 4 mm is located around the outer periphery of flange portion 14 of the lens blank, so that an annular groove is defined between convex portion 12 and the cylindrical frame member.

Meanwhile, 5% of C.I. Pigment Blue 15 (coloring agent; disperse dye) and 0.2% azobisisobutyronitrile (polymerization initiator) are added to methyl methacryate to prepare a polymerizable composition for the second polymerized material. The composition is poured into the annular groove provided on flange portion 14 of the lens blank. The lens blank is heated from 50° C. to 110° C. in eight hours, so as to polymerize the composition and thereby form a superposed layer on the lens blank.

Subsequently, the center of the lens blank is identified based on the outer periphery of convex portion 12, and this center is used as the center of working by a fraise. Thus, an intraocular lens including colored support portions is produced.

EXAMPLE 4

A rectangular lens blank having dimensions (unit: mm) indicated in FIG. 9 and including four convex portions 12, is formed of the same first polymerized material as that used in Example 1.

Meanwhile, 0.1% of C.I. Solvent Green 3 (coloring agent) and 0.2% azobisisobutyronitrile (polymerization initiator) are added to methyl methacryate to prepare a polymerizable composition for the second polymerized material. The composition is poured into an annular groove provided on flange portion 14 of the lens blank. The annular groove is covered with polyethylene film, and is kept at 50° C. for four hours. Thereafter, the temperature is raised from 50° C. to 110° C. in eight hours, so as to polymerize the composition and thereby form a superposed layer on the lens blank. From the rectangular lens blank, four disc-like lens blanks having a diameter of 20 mm are cut out such that each of the four lens blanks includes a convex portion 12 at a central part thereof and a double-layer portion surrounding the convex portion 12. The double layer portion consists of the flange portion 14 and the superposed layer formed of the second polymerized material.

Subsequently, the center of each lens blank is identified based on the outer periphery of convex portion 12, and this center is used as the center of working by a fraise. Thus, an intraocular lens including colored support portions is obtained.

EXAMPLE 5

A lens blank similar to that used in Example 1 is formed of the same first polymerized material as that used in Invention Example 1. Meanwhile, 0.1% of C.I. Solvent Violet 13 (coloring agent) and 0.8% of 2-methyl-2-hydroxy-1-phenylpropane-1-one (photopolymerization initiator) are added to methyl methacryate to prepare a polymerizable composition for the second polymerized material.

The thus prepared composition is poured into an annular groove provided on flange portion 14 of the lens blank. The annular groove is covered with polyethylene film, and is kept at a 20 cm distance under a 15 W ultraviolet (UV) lamp for eight hours, so as to polymerize the composition and thereby form on the lens blank a superposed layer of the second polymerized material.

Subsequently, the center of the lens blank is identified based on the outer periphery of protruding portion 16, and this center is used as the center of working by a fraise. Thus, an intraocular lens including colored support portions is produced.

While the present invention has been described in detail with respect to the presently preferred embodiments, it is to be understood that the present invention is by no means limited to the detailed particulars of the illustrated embodiments, and that the present invention may otherwise be embodied with various changes, improvements and modifications that may occur to those skilled in the art without departing from the spirit and scope of the invention defined in appended claims.

What is claimed is:

1. A process of producing a one-piece intraocular lens in which the intraocular lens includes an optical portion and at least one support portion produced integrally with each other, the process comprising the steps of:
    forming a first polymerized material into a lens blank, said lens blank including a central convex portion and a flange portion at least partially surrounding and extending radially outward from said convex portion, wherein said convex portion protrudes from one of two opposite major surfaces of the flange portion;
    forming a layer of monomer composition on said one of two opposite major surfaces of said flange portion, said monomer composition being polymerizable to produce a second polymerized material different from said first polymerized material, said monomer composition comprising at least one polymerizable monomer;
    polymerizing said monomer composition to provide a double-layer portion defined by said flange portion and said second polymerized material formed on said one of two opposite major surfaces of said flange portion; and
    forming said convex portion and said double-layer portion into said optical portion and said at least one support portion of the intraocular lens, respectively.

2. The process of claim 1, wherein said monomer composition further comprises a coloring agent.

3. The process of claim 1, wherein said monomer composition further comprises a dye which is polymerizable with said at least one monomer.

4. The process of claim 1, wherein said monomer composition further comprises a crosslinking agent.

5. The process of claim 1, wherein said lens blank includes a continuous thick portion protruding upward from an outer periphery of said flange portion of the lens blank, said convex portion and said continuous thick portion cooperating with said other to define a generally annular groove formed along said one of two opposite major surfaces of said flange portion.

6. The process of claim 1, wherein said lens blank is circular.

7. The process of claim 1, wherein said lens blank is rectangular.

8. The process of claim 1, wherein the top surface of said convex portion of said lens blank is partially spherical.

9. The process of claim 1, wherein said convex portion of said lens blank is cylindrical and has a top surface which is circular.

10. The process of claim 1, wherein said convex portion of said lens blank is substantially cylindrical and has a partially spherical top surface.

11. The process of claim 1, further comprising the step of applying a continuous frame member to an outer periphery of said flange portion of said lens blank, said convex portion and said frame member cooperating with each other to define a generally annular hollow space along said one of two opposite major surfaces of said flange portion.

12. The process of claim 1, wherein said at least one support portion is formed from said second polymerized material of said double-layer portion.

13. The process of claim 1, wherein said at least one support portion of the intraocular lens comprises a pair of J-shaped hooks which are opposite to each other with respect to said optical portion.

14. The process of claim 1, wherein said lens blank is formed as one-piece.

15. A process of producing a plurality of one-piece intraocular lenses, comprising the steps of:
    forming a first polymerized material into a lens blank, said lens blank including a plurality of convex portions, each convex portion being at least partially surround by a flange portion which extends radially outward from its respective convex portion, each convex portion protruding from one of two opposite major surfaces of each respective flange portion;
    forming a layer of a monomer composition on said one of two opposite major surfaces of each flange portion, said monomer composition being polymerizable to produce a second polymerized material different from said first polymerized material, said monomer composition comprising at least one polymerizable monomer;
    polymerizing said monomer composition to produce a double-layer portion defined by each flange portion and said second polymerized material formed on said one of two opposite major surfaces of each flange portion; and
    forming each convex portion and said double-layer portion into an optical portion and at least one support portion integral with said optical portion, respectively, thereby forming a plurality of intraocular lenses.

16. The process of claim 15, further comprising the step of separating said plurality of convex portions from each other such that each convex portion is surround by a corresponding double-layer portion.

* * * * *